United States Patent [19]
Attridge

[11] Patent Number: 5,631,170
[45] Date of Patent: May 20, 1997

[54] METHOD FOR IMPROVING MEASUREMENT PRECISION IN EVANESCENT WAVE OPTICAL BIOSENSOR ASSAYS

[75] Inventor: John W. Attridge, Woking, United Kingdom

[73] Assignee: Applied Research Systems ARS Holding N.V., Netherlands

[21] Appl. No.: 351,338

[22] PCT Filed: Jun. 9, 1993

[86] PCT No.: PCT/GB93/01217

§ 371 Date: Dec. 12, 1994

§ 102(e) Date: Dec. 12, 1994

[87] PCT Pub. No.: WO93/25908

PCT Pub. Date: Dec. 23, 1993

[30] Foreign Application Priority Data

Jun. 10, 1992 [GB] United Kingdom ............... 9212302

[51] Int. Cl.$^6$ .............. G01N 33/543; G01N 33/552
[52] U.S. Cl. .............. 436/518; 356/317; 356/318; 356/243; 356/246; 385/12; 385/129; 422/58; 422/61; 422/82.05; 422/82.08; 422/82.11; 422/57; 435/287.1; 435/287.2; 435/288.7; 435/808; 435/810; 435/967; 435/975; 436/164; 436/172; 436/527; 436/805
[58] Field of Search .............. 356/317, 318, 356/243, 246; 385/12, 129; 422/57, 58, 61, 82.05, 82.08, 82.11; 435/808, 810, 967, 975, 287.1, 287.2, 288.7; 436/164, 172, 518, 527, 535, 805, 807, 808, 809

[56] References Cited

U.S. PATENT DOCUMENTS

| | | | |
|---|---|---|---|
| 4,775,637 | 10/1988 | Sutherland et al. | 436/527 |
| 4,791,056 | 12/1988 | Sizto et al. | 435/4 |
| 4,978,503 | 12/1990 | Shanks et al. | 422/58 |
| 5,340,715 | 8/1994 | Slovacek et al. | 422/57 |

FOREIGN PATENT DOCUMENTS

| | | |
|---|---|---|
| 0093613 | 11/1983 | European Pat. Off. . |
| 103426 | 3/1984 | European Pat. Off. . |
| 171148 | 2/1986 | European Pat. Off. . |
| 9014590 | 11/1990 | WIPO . |
| 9209892 | 6/1992 | WIPO . |

OTHER PUBLICATIONS

Database WPI, Section Ch, Week 9119, Derwent Publications Ltd., London, GB; Class J04, AN 91-135984 & JP, A, 3 072 262 (Daikin KOgyo KKO, Mar. 27, 1991.

*Primary Examiner*—Christopher L. Chin
*Attorney, Agent, or Firm*—Ostrolenk, Faber, Gerb & Soffen, LLP

[57] ABSTRACT

A method for improving measurement precision in an optical biosensor assay for a ligand in a sample is described. The method involves referencing the assay with an artificially raised background level by the labelling of the optical waveguide with an appropriate reference reagent. Devices for use in such a method are also described.

19 Claims, 2 Drawing Sheets

FIG.6. —□— REFERENCE --○-- ASSAY SIGNAL --●-- RATIO

FIG.7. —□— REFERENCE --○-- ASSAY SIGNAL --●-- RATIO

METHOD FOR IMPROVING MEASUREMENT PRECISION IN EVANESCENT WAVE OPTICAL BIOSENSOR ASSAYS

BACKGROUND OF THE INVENTION

This invention relates to a method of improving measurement precision in optical biosensor assays employing evanescent wave detection, to devices for use in such a method and to the use of such devices.

DESCRIPTION OF THE PRIOR ART

Of the large variety of chemical and biochemical techniques used for analysis or assay, a particularly useful and sensitive one is an optical system employing the principles of internal reflection spectroscopy. Especially useful for immunoassays, such an optical system employs an optical waveguide, a portion of one surface of which generally carries an immobilised reagent, for example, a specific binding partner to the ligand to be assayed in the sample solution. A light beam directed into the waveguide will be totally internally reflected in the dense medium of the waveguide and will generate an electromagnetic waveform, known as the evanescent wave component at the surface of the waveguide. This component characteristically extends only a fraction of a wavelength across the interface between the waveguide and the sample solution. This penetration, however, is sufficient to permit substantial optical interaction between the evanescent wave component and entities close to or at the surface of the waveguide, and only minimal interaction with species in the bulk solution. Hence in the example of an immunoassay for a ligand where a specific binding partner to the ligand is immobilised onto the waveguide, the evanescent wave component will interact with this immobilised species and with any species complexed to it. By employing an optically labelled reagent in the assay which complexes with the immobilised species as a function of the amount of ligand present, the interaction of the evanescent wave component with this labelled reagent can be determined. Since there is only minimal interaction with the labelled reagent in the bulk solution, this then permits one to assay the ligand of interest. The two principal forms of optical detection which have been used are those based on the optical absorbance or fluorescence characteristics of the species to be measured i.e. Attenuated Total Reflection (ATR) and Total Internal Reflection Fluorescence (TIRF).

Such techniques and their application to assays are described, for example, by I. Chabay in Analytical Chemistry, Vol. 54. No. 9, (1982) and in EP-A-103426, and biosensors employing such techniques are described in, for example, Biosensors: fundamentals and applications, Eds. Turner, Karube and Wilson, pp. 655–678, OUP, 1987, Biosensors Vol. 1, 321–353, (1985), EP-A-171148 and WO-90/14590.

However, such optical assay systems suffer from two particular sources of imprecision which it would be desirable to reduce or eliminate. In particular, deficiencies in the surface quality of the waveguide, for example surface roughness, the overall flatness of the waveguide and the level of tilt of its surface relative to its longitudinal axis, will modulate the evanescent signal, these effects hereinafter being denoted as "edge effects"; these deficiencies will also lead to a scattering effect. In addition the intrinsic properties of the waveguide material and, for example, the presence of bulk inhomogeneities in the waveguide will also result in a scattering effect of the excitation light, of the signals from species in the bulk solution and the signals from species at or near the waveguide surface. Hence such edge effects and scattering effects, hereinafter collectively denoted "waveguide effects", can significantly affect the background signal of an assay system and the sensitivity range of an assay method, therefore introducing errors.

It is thus desirable to develop an assay method in which a reference measurement can be taken within the assay procedure in order to compensate for the various factors, such as those indicated above, which may alter the level of the observed assay measurement. An example of such a principle is illustrated in EP-A-093613 in which a reference signal is obtained from appropriate reagents in a discrete zone adjacent to the measurement zone.

However, adapting such a method would be of only limited applicability in terms of referencing for edge effects since these effects will be zone-dependent. Accordingly, for assays requiring high precision it is desirable to devise a method of achieving a reference signal from within the same zone of a biosensor as the measurement signal.

One possible way in principle of achieving this is to monitor the assay kinetics. This can be achieved by recording the rate of change of the assay signal which will be independent of waveguide effects. However, for certain assay procedures, the speed with which equilibrium is reached (for example with biosensor devices as described in WO-90/14590 competitive immunoassays typically reach equilibrium in less than 5 minutes), can introduce errors in the assessment of the rate of signal change as this rate will be critically dependent upon factors such as sample viscosity and temperature. In practice, therefore, this method has proved to be less precise than simply measuring the equilibrium signal of the assay.

Another possibility for referencing an assay would be to take a reference measurement from the desired zone before the assay has had time to start. For example, using biosensor devices as described in WO-90/14590 this can be achieved by delaying dissolution of fluorescently labelled assay specific reagents from the surface of the capillary gap remote from the waveguide. However, this initial measurement will necessarily be of very low intensity. In the example referred to earlier, this will be because the fluorophore used in the assay remains attached to the surface remote from the waveguide prior to addition of the sample. In certain cases, and in particular at wavelengths above 500 nm, signal contributions from the sample matrix reduce considerably bringing the detected background signal into the region where light scattering becomes a major contribution to the background signal. As this scattered signal is not generated by the same mechanism as the eventual assay signal, it will be subject to a different modulation by edge effects and the referencing will therefore be unreliable.

SUMMARY OF THE INVENTION

I have now devised a method of improving measurement precision in an optical biosensor assay employing evanescent wave detection which overcomes the problems outlined above. I have now found that the precision of a biosensor assay can be significantly improved by referencing the assay with an artificially raised background level by labelling of the optical waveguide with an appropriate reagent.

Thus, according to one aspect of the present invention I provide a method of improving measurement precision in an optical biosensor assay for a ligand in a sample which comprises the steps of i) incubating the sample in contact with a surface ("the measurement surface") which surface carries a directly or indirectly immobilised reagent ("the measurement reagent") appropriate to the assay technique employed and which surface additionally carries an amount of a directly or indirectly immobilised species ("the reference reagent") which gives rise to a detectable signal ("the reference signal"), independent of the amount of ligand present in the sample, at the measurement surface, and prior to, during, or subsequent to the said incubation of the sample, measuring the said reference signal by a method appropriate to the assay technique employed;

ii) simultaneously with or sequentially to the said incubation of the sample in i,) introducing one or more ancillary reagents appropriate to the assay technique employed whereby if ligand is present in the sample, a complex involving said measurement reagent and said ligand and/or said ancillary reagent(s) is formed giving rise to a detectable signal which is a first function of the amount of ligand (if any) present in the sample; and iii) subsequently monitoring the signal arising from the measurement surface ("the assay signal") by a method appropriate to the assay technique employed and, comparing the reference signal with the assay signal, thereby determining using an appropriate algorithm whether and/or the extent to which the ligand under assay is present in the sample.

The reference reagent is thus an optical label which is directly or indirectly immobilised onto the waveguide. This immobilisation can be achieved by techniques well known to the person skilled in the art; similarly in respect of the immobilisation of the measurement reagent. In a preferred embodiment, a mixture of labelled specific binding partner (i.e. the measurement reagent linked to the reference reagent) and unlabelled specific binding partner (i.e. the measurement reagent alone) to the ligand under assay is immobilised onto the measurement surface, allowing good control of the amount of reference reagent which becomes immobilised.

The reference signal will thus be either a) that obtained prior to incubation of the sample with the device or b) that obtained during or after incubation of the sample with the device but prior to the formation of a significant amount of complex at the measurement surface. Approach a) is more advantageous because the signal obtained will be affected only by those optical effects mentioned above (edge effects and scattering effects) arising from the waveguide i.e. it will be unaffected by any effects arising from the sample and/or any ancillary reagents present. Hence the variation in reference signal obtained from a given device by approach a) will be less than that obtained by approach b) i.e. the reference signal will be more reproducible and will be directed particularly to those sources of imprecision it is desired to reference for. However, given that the variations inherent in approach b) are only minor, this approach will also produce a valid result. In respect of approach b), in an ideal case, the reference signal will be that obtained prior to the formation of any complex at the measurement surface. However, in the case of simultaneous introduction of the ancillary reagents in step ii) above, this may be difficult to achieve. In this case, provided that at the time of measuring the reference signal only an insignificant amount of complex has formed at the measurement surface, i.e. an amount which will not significantly contribute to the measured signal, such a reference signal will yield a valid result. The assay signal will be equivalent to a combination of the reference signal and the signal arising from any complex formed at the measurement surface. The reference signal will thus be used to reference the assay signal i.e. including a signal obtained after a significant amount of complex has formed at the measurement surface. The reference signal will be modulated by edge effects in the same way as the subsequent assay signal(s). In addition, the reference signal, which acts as a background signal, is raised out of the region where scattering is a dominant effect, this scattering therefore being of less importance to the overall assay precision.

The assay method can, therefore, be carried out in a number of ways. In a two-stage method, the first stage involves measuring the reference signal. The second stage involves contacting the sample, already containing the ancillary reagents, with the measurement surface and subsequently measuring the assay signal. Alternatively, the first stage involves contacting the sample with the measurement surface and measuring the reference signal. The second stage involves the introduction of the ancillary reagents and subsequently measuring the assay signal. In a one-stage method, the sample, already containing the ancillary reagents, can be contacted with the measurement surface. The reference signal is measured shortly after this has occurred, but before a significant amount of complex has formed as a result of the assay reaction. Subsequently, measurement of the assay signal(s) may be taken.

Advantageously, use can also be made of time-delayed measurement of the reference and assay signals. In the case of using for example, fluorescently labelled species, included in the reference signal will be a component arising from the fluorescence of the reference reagent together with components arising from the intrinsic fluorescence of the waveguide and (depending on when the reference signal is measured) from the intrinsic fluorescence of the sample. Similarly, the assay signal will include a component from the reference reagent, the labelled ancillary reagent and from the intrinsic fluorescence of the waveguide/sample. All of these components will decay over time. The components arising from the intrinsic fluorescence of the waveguide/sample will, however, be of significantly lower intensity than the components arising from the fluorescently labelled reference reagent and ancillary reagent. Hence, by delaying the actual measurement of the signals (but of course, not delaying the excitation which gives rise to them), one can obtain a reference and assay signal arising solely from the labelled reagents i.e. when the components arising from the intrinsic fluorescence of the waveguide/sample have decayed to zero.

Various methods may be used to calibrate the assay signal by means of the reference signal. These methods can be summarised as either a subtractive, ratiometric, or a combined subtractive/ratiometric method. A simple ratiometric correction is, however, preferred.

The method of the present invention is applicable to a wide variety of indirect optical assay techniques, i.e. those in which optical labels are used, including competition assays and sandwich assays.

In sandwich assays, the detectable signal arising from the complex formed will in general be proportional to the quantity of ligand present in the sample. In competition assays, a complex between measurement reagent and ancillary reagent will be formed whether or not ligand is present in the sample but the detectable signal arising from this complex will depend on the quantity of ancillary reagent complexed; this will in general be inversely proportional to the quantity of ligand present in the sample.

Thus, in a competition assay according to a further embodiment of the present invention in steps i) and ii) either a) a labelled ligand analogue is present as an ancillary reagent and the measurement reagent (or optionally an ancillary reagent precomplexed with or capable of forming a complex involving the measurement reagent) is a specific binding partner for the ligand under assay or b) a labelled specific binding partner for the ligand under assay is present as an ancillary reagent and the measurement reagent (or optionally an ancillary reagent precomplexed with or capable of forming a complex involving the measurement reagent) is a ligand analogue.

In a sandwich assay according to a still further embodiment of the present invention, in step i) and ii) a labelled specific binding partner for the ligand under assay is present as an ancillary reagent and the measurement reagent (or optionally an ancillary reagent precomplexed with or capable of forming a complex involving the measurement reagent) is a further specific binding partner for the ligand under assay the said further specific binding partner being directed to an epitope of the ligand under assay different to the epitope to which the labelled specific binding partner is directed.

The term "ligand analogue" as used herein denotes a species which is capable of binding to the same epitopic site of the same specific binding partner as the ligand under assay, and includes inter alia within its scope a known amount of the ligand under assay or a labelled aliquot of the said ligand.

A wide variety of devices may be used to perform the method of the present invention including, for example, dipstick or "test-strip" biosensors, devices using a 'sample flow-through' configuration or devices employing sample containment. A preferred device to carry out the method of the present invention is a capillary fill device, especially a fluorescence capillary fill device, for example the type of device described in EP-A-171148 or in WO-90/14590. Such capillary fill devices may be used singly or in a suitable holder such as described in WO-90/1830.

As described in EP-A-171148, a capillary fill device (hereinafter CFD) typically consists of two plates of transparent material, e.g. glass, separated by a narrow gap or cavity. One plate acts as an optical waveguide and carries an immobilised reagent appropriate to the test to be carried out in the device. As described in WO-90/14590, the other transparent plate can carry on its surface remote from the cavity a layer of light-absorbing or opaque material. For use in a competition assay, the immobilised reagent may for example be a specific binding partner to the ligand desired to be detected and one of the plates may carry a dissoluble reagent comprising ligand analogue, labelled with a fluorescent dye (the ancillary reagent). When a sample is presented to one end of the CFD, it is drawn into the gap by capillary action and dissolves the ancillary reagent. In a competition assay for an antigen, the fluorescently labelled antigen analogue will compete with sample antigen for the limited number of antibody binding sites immobilised onto the waveguide. Because the capillary gap is narrow (typically about 100 microns), the reaction will generally go to completion in a short time, possibly less than 5 minutes depending upon the sample matrix and antibody affinity. Thus for a competition assay, the amount of fluorescently labelled antigen which becomes indirectly bound to the waveguide by virtue of complex formation will be inversely proportional to the concentration of antigen in the sample. In a sandwich assay, the waveguide will carry a specific binding partner for the ligand desired to be detected and one of the plates will carry a dissoluble reagent comprising a further specific binding partner labelled with a fluorescent dye (the ancillary reagent). In a sandwich immunoassay for an antigen, a sample antigen will form a sandwich complex with a fluorescently labelled antibody and an antibody immobilised on the waveguide. Thus, for a sandwich immunoassay, the amount of fluorescently labelled antibody which becomes indirectly bound to the waveguide by virtue of complex formation will be directly proportional to the concentration of antigen in the sample.

The term "antigen" as used herein will be understood to include both antigenic species (for example, proteins, bacteria, bacterial fragments, cells, cell fragments and viruses) and haptens which may be rendered antigenic under suitable conditions.

Thus, according to a further aspect of the present invention, I provide a specifically-reactive sample-collecting and testing device for use in an assay for a ligand as defined hereinbefore, possessing a cavity or cavities, one surface of the or each cavity having a zone I carrying a layer comprising, in releasable form, ancillary reagent(s) suitable for the desired assay, said surface being a surface of a first solid plate fashioned of transparent material, wherein the wall of the or each cavity opposite to said first plate comprises a second plate fashioned of transparent material and adapted to act as a light-transmissive waveguide, the second plate having on its surface adjacent the cavity a zone II corresponding in orientation to the aforementioned zone I, zone II carrying a layer comprising, randomly distributed, an immobilised measurement reagent and an immobilised reference reagent, both as hereinbefore defined, suitable for the desired assay. The first plate advantageously carries on its external face an opaque coating.

Hence in such a device, the reagent(s) carried by zone I are the ancillary reagent(s) in soluble releasable form and the reagents carried by zone II are the immobilised measurement reagent and reference reagent in admixture.

CFDs for use in the method of the invention may if desired contain multiple assay zones enabling simultaneous or sequential assays for different ligands in the same sample to be conducted.

Alternatively, for the purposes of quantitative calibration, the multiple assay zones may be configured to contain different known amounts of the ligand under assay. For example, for a competition assay for a ligand, in a situation where the device contains three assay zones, the first zone may, for example, contain a labelled amount of a ligand analogue as an ancillary reagent. The second and third zones may, for example, each contain an amount of a labelled ligand analogue as an ancillary reagent together with a known amount (different for each of the two zones) of the ligand under assay. The measurement reagent and reference reagent will be the same for all three zones. Hence, the assay signal from the first zone will be a function of the amount of ligand in the sample. The assay signals from the second and third zone will be reduced as compared to that from the first zone due to the presence of the extra amount of ligand. The reduction will be related to the amounts of ligand used as ancillary reagent in each of the zones. Hence, this will enable quantitative calibration to be performed. Analogously, for a sandwich assay, the presence of ligand as an ancillary reagent in the second and third zones will give an increase in the assay signal from these zones as compared to that from the first zone.

The identities of the reagents used will depend both on the ligand to be assayed and on the assay methodology and will be clearly apparent to the skilled person. As indicated above, the reference reagent provides an initial signal and is simply a label, for example a fluorescent label. Preferably, the reference reagent is a fluorescent label which is directly attached to the measurement reagent.

The ancillary reagent(s) in the measurement region are preferably contained within a dissoluble layer of a suitable material. After deposition of the soluble reagent(s), a capping layer e.g. polyvinyl alcohol (PVA) may be placed upon the reagent, which capping layer delays the dissolution of the reagent for a few seconds after the addition of the sample to the device. In respect of the measurement region, this delayed release of the ancillary reagent(s) presents an ideal opportunity to measure the reference signal and thus this embodiment is likely to provide for more accurate referencing for waveguide effects than if the ancillary reagent(s) is (are) present initially in the sample.

Capillary fill devices according to the invention may be manufactured by methods broadly similar to those described in EP-A-171148.

Thus, according to the present invention we also provide a method of manufacturing specifically-reactive sample-collecting and testing devices as described hereinbefore comprising the steps of (a) forming a patch of suitable reagent(s), carried by zone I, as described hereinbefore on the surface of a sheet material which is to provide part of a multiplicity of the devices, (b) forming a patch of suitable reagent(s), carried by zone II, as described hereinbefore on the surface of an additional structure, involving the immobilisation of the measurement reagent and reference reagent, as described hereinbefore, said additional structure together with the said sheet material providing for each of the multiplicity of devices a cavity for collecting and retaining a volume of sample liquid in contact with the said layers of suitable reagents, the cavity preferably being of capillary dimension, and (c) separating the sheet material into portions each providing one or a plurality of the sample-collecting and testing devices.

Although the preceding discussion is made with particular reference to fluorescent labels, it will be appreciated that it also applies to reagents conjugated to labels which exhibit other properties (e.g. phosphorescence or luminescence).

Examples of fluorophores which may be used in the method of assay according to the invention include, but are not restricted to, fluorescein and its derivatives (e.g. fluorescein isothiocyanate (FITC)), rhodamine and its derivatives (e.g. XRITC, TRAP, TRITC), lucifer yellow, 2,4-dinitrofluoro-benzene, phenylisothiocyanate, dansyl chloride, phycobiliproteins (e.g. allophycocyanin and phycoerythrin) and indocyanins.

The label used for the reference reagent may be different to that carried by the ancillary reagent(s). However in this particular embodiment, certain disadvantages are apparent. In particular, the cost and complexity of the instrumentation will be greater as either two sets of interchangeable filters will be required or two monochromatic light sources will be required. Also, the two labels must both have the same required properties for an assay e.g. pH stability and temperature stability. The sensitivity of the assay signal may also be compromised by signal crosstalk from the reference label due to spectral overlap of the two labels. It is possible to select two different labels in which these disadvantages are not present or are minimal; however, it is preferable to use the same label for both the reference reagent and the ancillary reagent(s).

A further advantage of the present invention is that the use of a reference reagent on the measurement surface enables a quality assurance/quality control check to be made on the biosensor device. In particular, the success of the immobilisation of the reference reagent and thus, in turn, of the measurement reagent can be assessed by measuring the signal arising from the device without sample present. The reproducibility of a particular signal value can then be used to reject devices in which immobilisation has been incomplete.

As indicated previously, the method according to the present invention is principally directed to the compensation of waveguide effects. However, it would be advantageous to additionally compensate for other factors in an assay system which may influence the level of signal observed. Current assay techniques are highly sensitive to temperature, reagent stability, incubation and development time and other conditions and interfering factors which may affect the level of signal observed. This additional compensation can be achieved, by using an assay method as hereinbefore described in which additional separate calibration step(s) are carried out. In such a method, a device is used which is provided with appropriate reagents disposed in one or more regions (calibration region(s)) separate from the region containing the measurement reagent and reference reagent. The concept of using calibration regions for such compensation is described in detail in International Patent Application No. PCT/GB91/02058.

The use of such additional calibration step(s) will serve two main purposes, namely i) to confirm that the various reagents used in the assay procedure are performing according to their specification, and ii) to define a certain concentration level within the sample on test, and thereby to compensate for background interference (e.g. background fluorescence), temperature and pH changes and other factors originating from the sample matrix which may alter the level of the observed signals.

Thus, an embodiment of the method of assay as hereinbefore defined is provided additionally comprising the steps of iv) simultaneously or sequentially to the incubation in step i), incubating the sample, if desired together with one or more ancillary reagents, with one or more further surface(s) ("the calibration surface(s)") onto each of which is immobilised a reagent ("the calibration reagent") appropriate to the assay technique employed, the calibration reagent either being such to give rise to a zero or non-zero signal or being such as to form a complex involving said ligand and/or said ancillary reagent(s) whereby any such complex gives rise to a non-zero signal (or, where no such complex is formed, which would be formed if ligand were present), the signal being either a second function of or independent of the amount of ligand (if any) present in the sample;

v) monitoring the signal(s) ("the calibration signal(s)") arising from the calibration surface(s); and vi) subsequently comparing the calibration signal(s) to both the assay signal and reference signal as hereinbefore defined and, using an appropriate algorithm, the measure of the extent to which the ligand under assay is present in the sample, as derived from the assay signal and reference signal is thereby calibrated.

In embodiments of the method wherein at a calibration surface there occurs a binding reaction analogous to that which occurs at the measurement surface (if ligand is present in the sample), purpose i) indicated above is achieved i.e. there may be confirmation that the reagents in the complex which give rise to the signal have not degraded or that the binding reactions are occurring satisfactorily i.e.

the binding partners in such reactions have not degraded. Purpose ii) may also be achieved in these embodiments.

In the embodiments of the method wherein at a calibration surface the calibration reagent gives rise to the desired non-zero signal without there being a binding reaction to any ancillary reagent(s), purpose ii) indicated above is achieved.

In step iv) above, where the signal is a second function of the amount of ligand present in the sample, this second function is different to the first function specified in step ii).

Where more than one calibration surface is present, the calibration reagents on each will generally be chosen such that the signals arising from each calibration surface are not identical. Such non-identical signals can arise where the signal arising from each calibration surface is the same function of the amount of ligand present in the sample. One example is where the calibration reagents on each calibration surface are the same but the amounts of ancillary reagent(s) which form a complex with the calibration reagents on each surface differ. Another example is where the calibration reagents on each calibration surface each give rise to a signal without the need for an ancillary reagent and are present in differing amounts. If it is found, despite such a choice of calibration reagents that identical signals arise, then device failure (e.g. due to extremes of sample pH, too high a sample background signal or reagent degradation) is indicated and the assay can be rejected; this is a further advantage of the present invention.

The term "zero signal" as used above denotes the background signal for the assay concerned. The term "non-zero signal" is to be construed accordingly.

In a direct or sandwich assay, the zero signal will be the signal obtained when no analyte is present. In a competition assay, the zero signal will be the signal corresponding to the low asymptote of the appropriate assay curve and will therefore not be the signal obtained when no analyte is present.

Various methods may be used to calibrate the assay signal by means of the calibration signal(s). These methods can be summarised as either an additive, multiplicative or a combined additive/multiplicative method. All methods rely on characterisation of the calibration region(s) during manufacture, so that any difference measured at the time of assay can be used to correct the data from the measurement region.

In a competition assay according to a further embodiment of the present invention in which one or more additional calibration step(s) are carried out as hereinbefore described, in step iv) either a) a labelled ligand analogue is present as an ancillary reagent and the calibration reagent (or optionally an ancillary reagent precomplexed with or capable of forming a complex involving the calibration reagent) is a specific binding partner for the ligand under assay or b) a labelled specific binding partner for the ligand under assay is present as an ancillary reagent and the calibration reagent (or optionally an ancillary reagent precomplexed with or capable of forming a complex involving the calibration reagent) is a ligand analogue or c) a labelled ligand distinct from the ligand under assay is present as an ancillary reagent and the calibration reagent (or optionally an ancillary reagent precomplexed with or capable of forming a complex involving the calibration reagent) is a specific binding partner for the ligand distinct from the ligand under assay or d) the calibration reagent is a binding partner non-specific for any ancillary reagent(s) present or e) the calibration reagent gives rise to the desired zero or non-zero signal without the need for the presence of an ancillary reagent.

In a sandwich assay according to a further embodiment of the present invention in which one or more additional calibration step(s) are carried out as hereinbefore described, in step iv) either a) the calibration reagent (or optionally an ancillary reagent precomplexed with or capable of forming a complex involving the calibration reagent) is a specific binding partner for the ligand under assay, a labelled specific binding partner for the ligand under assay is present as an ancillary reagent and a known amount of the ligand under assay precomplexed to its labelled specific binding partner is present as a yet further ancillary reagent or b) a labelled specific binding partner for the ligand under assay is present as an ancillary reagent and the calibration reagent (or optionally an ancillary reagent precomplexed with or capable of forming a complex involving the calibration reagent) is a known amount of the ligand under assay precomplexed to its immobilized specific binding partner or c) a ligand distinct from the ligand under assay is present as an ancillary reagent and the calibration reagent (or optionally an ancillary reagent precomplexed with or capable of forming a complex involving the calibration reagent) is a labelled specific binding partner for the ligand distinct from the ligand under assay or d) the calibration reagent is a labelled binding partner non-specific for any ancillary reagent(s) present or e) the calibration reagent gives rise to the desired zero or non-zero signal without the need for the presence of an ancillary reagent.

A wide range of possibilities present themselves for the configuration of the calibration regions for use in the method of the present invention. These possibilities are set out in detail in International Patent Application No. PCT/GB91/02058, incorporated herein by reference.

Thus according to a further aspect of the present invention, I provide a device for use in an assay in which one or more additional calibration step(s) are carried out as hereinbefore described, being a specifically-reactive sample-collecting and testing device as defined hereinbefore additionally carrying on said first plate one or more further zone(s) carrying a layer comprising, in soluble releasable form, ancillary reagent(s) suitable for the desired assay and additionally carrying on said second plate one or more further zone(s) each of which is corresponding in orientation to one of said further zone(s) on said first plate, and each of which is carrying a layer comprising an immobilised calibration reagent as hereinbefore defined.

Thus CFDs for use in an assay in which one or more additional calibration step(s) are carried out are as hereinbefore described but with one or more calibration region(s) as indicated above. Again, a wide range of possibilities of calibration regions for use in such CFDs present themselves. These possibilities are set out in detail in International Patent Application No. PCT/GB91/02058, incorporated herein by reference.

Manufacture of the CFDs possessing one or more calibration region(s) as described above may be carried out by an analogous method to that described hereinbefore for CFDs possessing only zones I and II, by additionally forming the patch of suitable reagents in the further zone(s) on the surface of the sheet material and immobilising the calibration reagent in the further zone(s) on the surface of the additional structure.

The method of the invention is particularly applicable to assays of antigens or antibodies, i.e. to immunoassays, and in a preferred embodiment of the invention the ligand is an antigen and the specific binding partner comprises an antibody to the said antigen. However, the invention is not to be taken as limited to assays of antibodies or antigens. Examples of ligands which may be assayed by the method of the invention are given in Table 1 below, together with an indication of a suitable specific binding partner in each instance.

TABLE 1

| Ligand | Specific Binding Partner |
| --- | --- |
| antigen | specific antibody |
| antibody | antigen |
| hormone | hormone receptor |
| hormone receptor | hormone |
| Polynucleotide strand | complementary polynucleotide strand |
| avidin | biotin |
| biotin | avidin |
| protein A | immunoglobulin |
| immunoglobulin | protein A |
| enzyme | enzyme cofactor (substrate) or inhibitor |
| enzyme cofactor (substrate) or inhibitor | enzyme |
| lectins | specific carbohydrate |
| specific carbohydrate of lectins | lectins |

The method of the invention has very broad applicability but in particular may be used to assay: hormones, including peptide hormones (e.g. thyroid stimulating hormone (TSH), luteinizing hormone (LH), human chorionic gonadotrophin (hCG), follicle stimulating hormone (FSH), insulin and prolactin) or non-peptide hormones (e.g. steroid hormones such as cortisol, estradiol, progesterone and testosterone, or thyroid hormones such as thyroxine (T4) and triiodothyronine), proteins (e.g. carcinoembryonic antigen (CEA) and antibodies and alphafetoprotein (AFP)), drugs (e.g. digoxin, drugs of abuse), sugars, toxins, vitamins, viruses such as influenza, parainfluenza, adeno-, hepatitis, respiratory and AIDS viruses, virus-like particles or microorganisms.

It will be understood that the term "antibody" used herein includes within its scope:

(a) any of the various classes or sub-classes of immunoglobulin, e.g. IgG, IgA, IgM, or IgE derived from any of the animals conventionally used, e.g. sheep, rabbits, goats or mice, (b) monoclonal antibodies, (c) intact molecules or "fragments" of antibodies, monoclonal or polyclonal, the fragments being those which contain the binding region of the antibody, i.e. fragments devoid of the Fc portion (e.g. Fab, Fab', F(ab')$_2$), the so-called "half-molecule" fragments obtained by reductive cleavage of the disulphide bonds connecting the heavy chain components in the intact antibody or fragments obtained by synthetic methods, (d) antibodies produced or modified by recombinant DNA techniques.

The method of preparation of fragments of antibodies is well known in the art and will not be described herein.

The term "antigen" as used herein will be understood to include both permanently antigenic species (for example, proteins, bacteria, bacterial fragments, cells, cell fragments and viruses) and haptens which may be rendered antigenic under suitable conditions.

The present invention further provides apparatus suitable for use in the method of assay according to the invention as hereinbefore described which comprises a device according to the invention as hereinbefore defined; a source of radiation capable of being arranged such that, in use, radiation enters the said device such that optically labelled species in the device are excited; and means for monitoring the emerging radiation.

In a further embodiment, the device can be illuminated via a mask, thereby defining the effective volume of the device in which the binding reaction occurs. The effective volume is the product of the distance between base and top plates of the device and the area of the illumination zone as defined by the mask in the optical train.

The present invention further provides a kit for performing a method of assay according to the present invention comprising a device as hereinbefore defined together with appropriate ancillary reagents.

DESCRIPTION OF THE DRAWINGS

For a better understanding of the present invention, reference is made to the accompanying drawings wherein:

In FIGS. 2 to 5, the symbols illustrated denote the following entities:

Antigen under assay

*— fluorescent label

*— fluorescently labelled antigen analogue

—( or —( specific antibody to antigen under assay

☐ antigen distinct from antigen under assay

—< specific antibody to specific antibody to antigen under assay.

DETAILED DESCRIPTION

Figure 1:
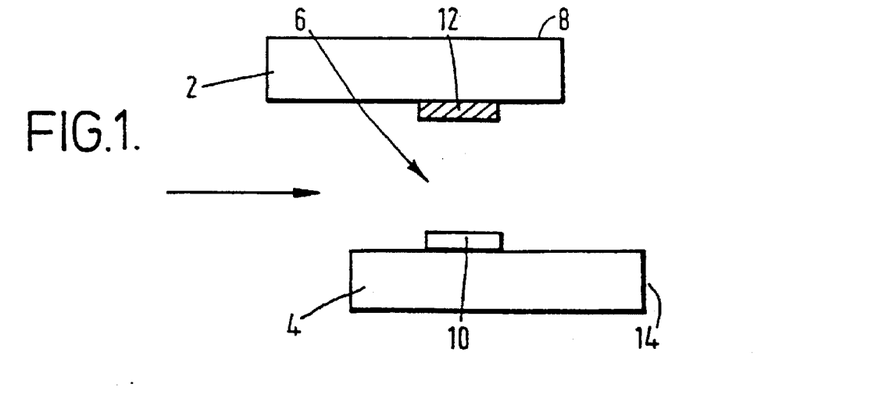
FIG. 1 shows a diagrammatic section through a fluorescence capillary fill device (hereinafter FCFD) according to one embodiment of the present invention.

Referring to FIG. 1, the device depicted comprises an upper plate 2 fashioned of transparent material (e.g. of plastic material, quartz, silica or glass) carrying on its external face an opaque coating 8, and a lower plate 4 fashioned of transparent material, both plates being around 1 mm thick and fixed together in substantially parallel relationship, less than 1 mm apart by means of bonding tracks of suitable adhesive containing spacer means (not shown). In the embodiment shown, the cell cavity 6 so formed is open to the surroundings at both ends, so that when liquid sample is drawn into one opening of the cavity by means of capillarity, air may escape through the other opening. In the embodiment shown, the two plates are offset, although this is not a necessary feature of the device.

Carried on the inner surface of the upper plate 2 is a patch of reagent(s) appropriate to the test being carried out, being carried by zone I (12) as defined hereinbefore. The reagent(s) are contained within the device in a soluble releasable form.

Carried on the inner surface of the lower plate 4 is a patch of reagent appropriate to the test being carried out, being carried by zone II (10) as defined hereinbefore, said zone 10 being directly below zone 12 on the plate 2. In the case of an immunoassay, the zone 10 will carry, for example, an amount of labelled and unlabelled relevant immobilised antibody or antigen or hapten.

The operation in use of an embodiment of the device shown in FIG. 1 will now be described. Although the following description relates to the use of a device in a labelled-antigen format competition-type immunoassay, it should be understood that devices according to the invention are also suitable for use in labelled-antibody format immunoassays (both competition-type and sandwich-type) and in other types of assay (sandwich-type or competition-type) or in other types of chemical or biochemical tests.

The sample liquid passes into the device in the direction of the arrow shown in FIG. 1. A short time after the cavity 6 fills with sample liquid, the patch 12 of material dissolves, releasing the reagents contained therein into the liquid.

As mentioned hereinbefore, the patch 12 may be carried on the upper plate 2 by means of suitable dissoluble material (s). Suitable dissoluble materials include humectant coatings, e.g. sucrose- or sorbitol-based. A further optional feature is to coat the patch 12 with a thin layer of a material which provides some delayed release of the reagents within the patches. Suitable materials for coating the patch. include, for example, polyvinyl alcohol (PVA). A suitable PVA coating would take typically 2–10 seconds to dissolve after initial contact of a sample liquid.

In one embodiment of the device of the type shown in FIG. 1 which is set up for a competition-type immunoassay for an antigen, patch 12 may contain a fluorescently labelled antigen analogue. Patch 10 would then comprise an amount of fluorescently labelled and unlabelled immobilised specific binding partner being a specific antibody to the antigen under assay. Thus, upon introduction of the sample liquid, the patch 12 dissolves, releasing antigen analogue into the sample liquid. Antigen introduced in the sample liquid competes with antigen analogue for epitopic binding sites on the specific antibody to the antigen contained in patch 10. The amount of fluorescent material which becomes bound to the immobilised specific antibody in patch 10 will therefore be a function of the concentration of antigen in the sample liquid. Conventional competition-type optical immunoassays involve this type of competitive equilibrium.

The total amount of fluorescent material bound to the patch 10 at a particular moment will therefore be the sum of that present initially in patch 10 from the reference reagent with that originating from the reagent(s) in patch 12.

Figure 2:
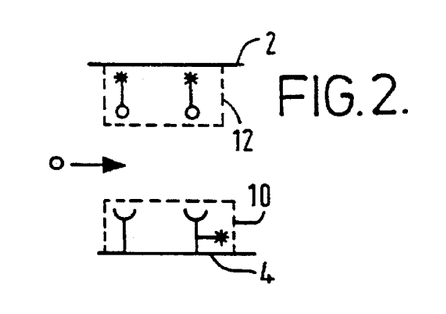
FIG. 2 illustrates schematically an example of the measurement region in an embodiment of the preferred device according to the invention for a competition assay.

For this first embodiment, the measurement region and the reagents contained therein are illustrated schematically in FIG. 2.

Figure 3:
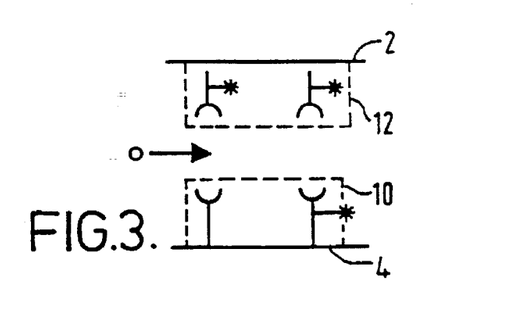
FIG. 3 illustrates schematically an example of the measurement region in an embodiment of the preferred device according to the invention for a sandwich assay.

For a sandwich assay embodiment of the device hereinbefore described, an example of the measurement region and the reagents contained therein is illustrated in FIG. 3.

In both of the examples hereinbefore described, the same fluorescent species is used as a fluorescent label on those reagents stated to be labelled.

Accordingly, a reference signal measurement is taken after the sample liquid has filled the cavity 6. Assay signal measurement is taken once assay equilibrium has been established. The optical signals arising from the fluorescent species in zone 10 will emerge from the optical edge 14 and be detected by an optical detector before being processed in a desired manner. A measure of the amount of ligand present in the sample is obtained by a suitable method, preferably by ratiometric correction of the assay signal using the reference signal.

Figure 4:
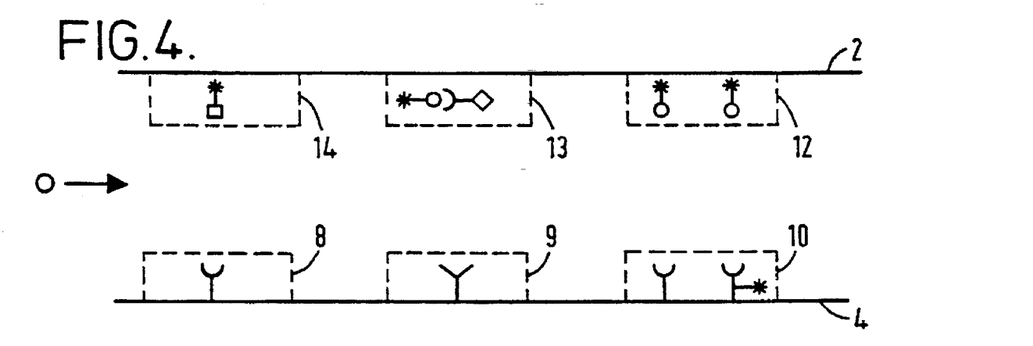
FIG. 4 illustrates schematically an example of an FCFD possessing two calibration regions according to one embodiment of the present invention.

In FIG. 4, the device depicted comprises an upper plate 2, and a lower plate 4 as in the device of FIG. 1. Carried on the inner surface of plate 2 is a zone 12 and carried on the inner surface of plate 4 is a zone 10, these zones and the reagents contained therein being as described above in respect of FIG. 1. Zones 9 and 13 and zones 8 and 14 carried on plates 2 and 4 as shown comprise two different calibration regions as described hereinbefore. In use, in the region bounded by the pair of zones 9 and 13 an initial high signal will arise from the zone 9 due to the binding of the complex in zone 13 to the immobilised reagent in zone 9. This signal will decrease over time as ligand competes with the labelled ligand analogue in the complex in patch 9. In use, in the region bounded by the pair of zones 8 and 14, a zero signal will arise from the zone 8 since the labelled species in zone 14 will not bind to the immobilised reagent in zone 8. The signals arising from zones 8 and 9 will be used to calibrate that from zone 10. Hence, using the terminology of PCT Application. No. PCT/GB91/02058, the region bounded by zones 9 and 13 will be a high signal calibration region and the region bounded by zones 8 and 14 will be a zero signal calibration region. Further possibilities for calibration regions for the device according to the present invention are illustrated in PCT Application No. PCT/GB91/02058, collectively described therein as calibration regions and auxiliary calibration regions.

Figure 5:
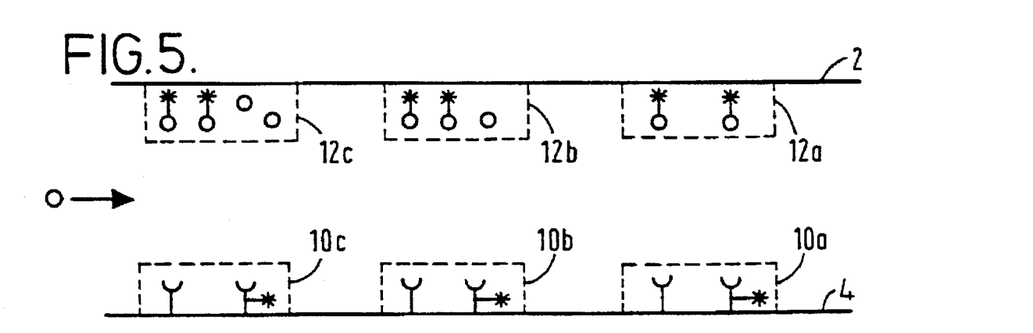
FIG. 5 illustrates schematically an example of an FCFD possessing multiple assay zones for quantitative calibration according to one embodiment of the present invention.

In FIG. 5, the device depicted comprises an upper plate 2 and a lower plate 4, as in the device of FIG. 1. The lower plate 4 carries three zones, 10a, 10b, and 10c, each of which and the reagents contained therein being as in zone 10 described above in respect of FIG. 1. The upper plate carries three zones 12a, 12b and 12c, each of these zones carrying reagents as in zone 12 described above in respect of FIG. 1. Zones 12b and 12c additionally carry different known amounts of ligand. Hence in use, the reference signal from each zone 10a, 10b and 10c is recorded prior to the release of reagents from zones 12a, 12b and 12b. Subsequently, the reagents in zones 12a, 12b and 12c are released and assay signals are recorded from each of zones 10a, 10b and 10c. Due to the presence of the amounts of ligand in zones 12b and 12c, the assay signals arising from zones 10b and 10c will be of reduced intensity compared to that arising from zone 10a. This enables quantitative calibration of the device to be achieved.

The following Example serves to illustrate the applicability of the method of the present invention without, however, limiting it.

EXAMPLE 1

FITC-labelled and unlabelled αLH-antibody were immobilised in different proportions onto the plate acting as the waveguide of a number of fluorescence capillary fill devices. 10 devices were employed at each of the concentrations of labelled antibody used. Each device was then filled with serum and a reference signal was recorded. Each device was then washed through with a premixed solution of αLH-TRAP conjugate and LH at 1250 mIU/ml and an assay signal was recorded after equilibrium had been established (after approximately 15 minutes incubation).

Measurements were made at wavelengths suitable for the TRAP fluorophore. In this case, there is sufficient crosstalk from FITC to give a measurable reference signal at this wavelength, particularly at the higher incorporation ratios. The results are summarised in Table 2 below:

TABLE 2

| | % CV's for TRAP-assay | | |
| --- | --- | --- | --- |
| | | Signal Precision | |
| % labelled - αLH loading | Serum (reference) signal | Assay signal | Referenced Assay Signal |
| 0.2 | 10.9 | 15.6 | 7.0 |
| 0.5 | 13.2 | 18.4 | 10.2 |
| 1.0 | 12.7 | 18.1 | 4.2 |
| 2.5 | 17.6 | 23.3 | 3.3 |
| 6.1 | 31.3 | 36.7 | 3.7 |

These results show that the precision of the referenced assay signal (as determined by the ratio of the reference and assay signals) is greater than that of the individual signals. The ability to reference poor signal precision increases with the proportion of immobilised label, with dramatic improvements in precision being found at higher concentrations where the influence of the glass background variability is reduced, the referenced signal precisions being improved to a % CV value of less than 4%. The fact that a ratiometric correction is more effective than a subtractive correction illustrates that it is the waveguide effects and not other background effects that are being corrected for.

Figure 6:
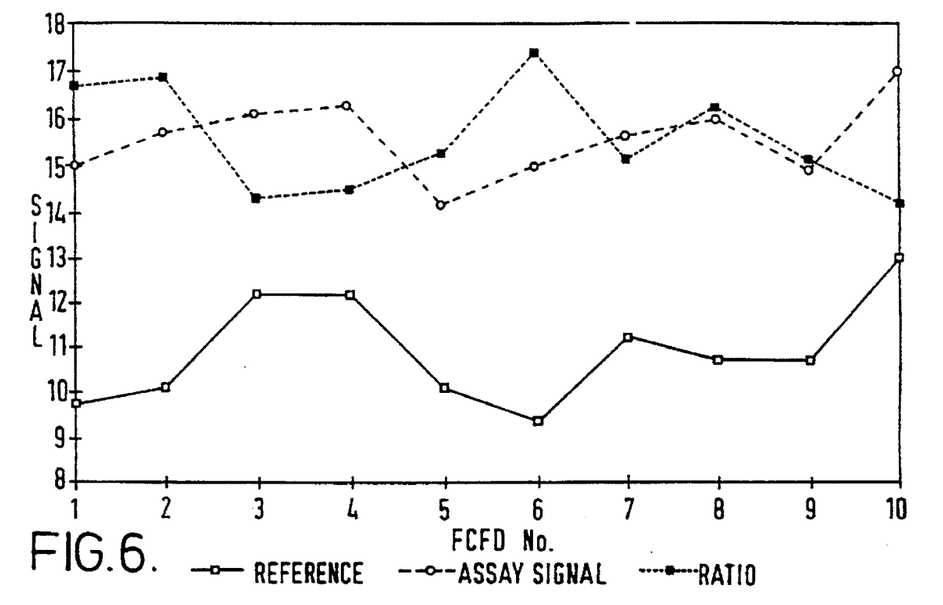
FIGS. 6 and 7 show results of devices tested at 2 extreme levels of labeling.
Figure 7:
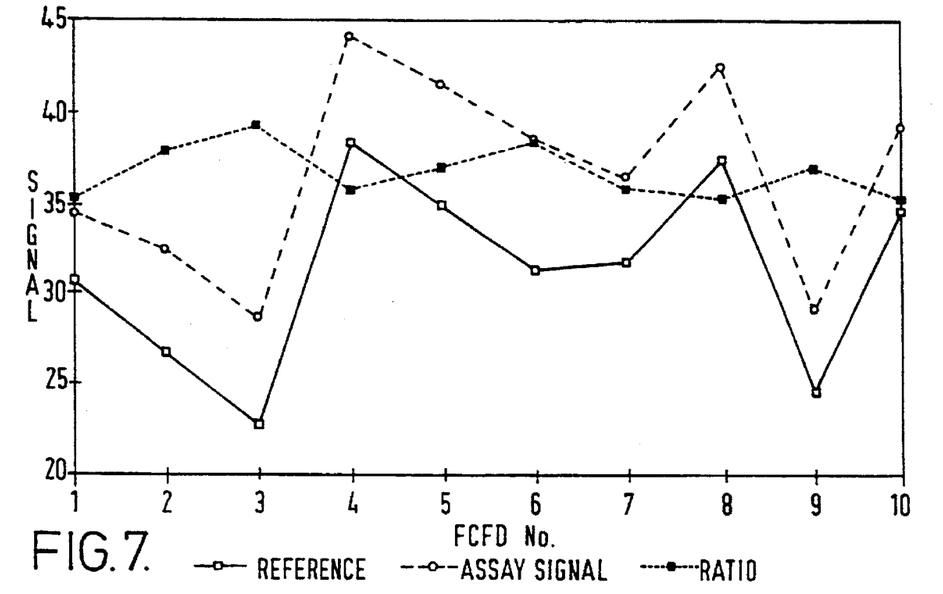

The results from each of the devices tested for the two extreme levels of labelling are shown in FIGS. 6 and 7 and illustrate the method of referencing. At low levels of labelling (0.2%), FIG. 6, the signal variability is predominantly influenced by scattering of the excitation light into the detection system. The scattering varies from measurement to measurement and, hence, there is no real correlation between the assay and reference signals. As a result, the ratio of the signals shows approximately the same variation as the two independent signals. At a higher level of labelling (6%), FIG. 7, signals are raised and scattering has less of an influence on the signal variability. Edge effects now dominate signal precision and affect both the reference and assay signals equally. These two signals are now correlated and a ratio of the two shows better precision than was obtained for either of the individual signals. The precision is also better than that achieved with the previous low level of labelling.

I claim:

1. A method of improving measurement precision in an optical biosensor assay for a ligand in a sample which comprises the steps of
    i) incubating the sample in contact with a measurement surface which carries a directly or indirectly immobilised measurement reagent appropriate to the assay and which additionally carries an amount of a directly or indirectly immobilised reference reagent which gives rise to a reference signal, independent of the amount of ligand present in the sample, at the measurement surface, and prior to, during, or subsequent to the said incubation of the sample measuring said reference signal by a method appropriate to the assay;
    ii) simultaneously with or sequentially to the said incubation of the sample in i) introducing one or more labelled ancillary reagents appropriate to the assay whereby if ligand is present in the sample, a complex involving said measurement reagent and at least one of said ligand or said labelled ancillary reagent(s) is formed giving rise to a detectable assay signal which is a first function of the amount of ligand (if any) present in the sample; and
    iii) subsequently monitoring the assay signal arising from the measurement surface by a method appropriate to the assay and, comparing the reference signal with the assay signal, thereby determining using an appropriate algorithm whether and/or the extent to which the ligand under assay is present in the sample.

2. A method as claimed in claim 1 additionally comprising the steps of
    iv) simultaneously or sequentially to the incubation in step i), incubating the sample, if desired together with one or more labelled ancillary reagents, with one or more further calibration surface(s) separated from the measurement surface onto each of which is immobilised a calibration reagent appropriate to the assay, the calibration reagent either being such to give rise to a zero or non-zero signal or being such as to form a complex involving at least one of said ligand or said labelled ancillary reagent(s) whereby any such complex gives rise to a non-zero signal (or, where no such complex is formed, which would be formed if ligand were present), the signal being either a second function of or independent of the amount of ligand (if any) present in the sample;
    v) monitoring the calibration signal(s) arising from the calibration surface(s); and
    vi) subsequently comparing the calibration signal(s) to both the assay signal and reference signal and, using an appropriate algorithm, the measure of the extent to which the ligand under assay is present in the sample, as derived from the assay signal and reference signal is thereby calibrated.

3. A method as claimed in claim 2, the assay being a competition assay, wherein in steps i) and ii) either a) a labelled ligand analogue is present as a labelled ancillary reagent and the measurement reagent (or optionally a reagent precomplexed with or capable of forming a complex involving the measurement reagent) is a specific binding partner for the ligand under assay or b) a labelled specific binding partner for the ligand under assay is present as a labelled ancillary reagent and the measurement reagent (or optionally a reagent precomplexed with or capable of forming a complex involving the measurement reagent) is a ligand analogue; and wherein in step iv), either a) a labelled ligand analogue is present as a labelled ancillary reagent and the calibration reagent (or optionally a reagent precomplexed with or capable of forming a complex involving the calibration reagent) is a specific binding partner for the ligand under assay or b) a labelled specific binding partner for the ligand under assay is present as a labelled ancillary reagent and the calibration reagent (or optionally a reagent precomplexed with or capable of forming a complex involving the calibration reagent) is a ligand analogue or c) a labelled ligand distinct from the ligand under assay is present as a labelled ancillary reagent and the calibration reagent (or optionally a reagent precomplexed with or capable of forming a complex involving the calibration reagent) is a specific binding partner for the ligand distinct from the ligand under assay or d) the calibration reagent is a binding partner non-specific for any labelled ancillary reagent(s) present or e) the calibration reagent gives rise to the desired zero or non-zero signal without the need for the presence of a labelled ancillary reagent.

4. A method as claimed in claim 2, the assay being a sandwich assay, wherein
    in step i) and ii) a labelled specific binding partner for the ligand under assay is present as a labelled ancillary reagent and the measurement reagent (or optionally a reagent precomplexed with or capable of forming a complex involving the measurement reagent) is a further specific binding partner for the ligand under assay, said further specific binding partner being directed to an epitope of the ligand under assay different to the epitope to which the labelled specific binding partner is directed;

and wherein in step iv), either a) the calibration reagent (or optionally a reagent precomplexed with or capable of forming a complex involving the calibration reagent) is a specific binding partner for the ligand under assay, a labelled specific binding partner for the ligand under assay is present as a labelled ancillary reagent and a known amount of the ligand under assay precomplexed to its labelled specific binding partner is present as a yet further ancillary reagent or b) a labelled specific binding partner for the ligand under assay is present as a labelled ancillary reagent and the calibration reagent (or optionally a reagent precomplexed with or capable of forming a complex involving the calibration reagent) is a known amount of the ligand under assay precomplexed to its immobilized specific binding partner or c) a ligand distinct from the ligand under assay is present as an ancillary reagent and the calibration reagent (or optionally a reagent precomplexed with or capable of forming a complex involving the calibration reagent) is a labelled specific binding partner for the ligand distinct from the ligand under assay or d) the calibration reagent is a labelled binding partner non-specific for any labelled ancillary reagent(s) present or e) the calibration reagent gives rise to the desired zero or non-zero signal without the need for the presence of a labelled ancillary reagent.

5. A method as claimed in claim 1 wherein time-delayed measurement of the reference signal and assay signal is made.

6. A method as claimed in claim 1 wherein the reference signal, assay signal and calibration signal(s), when present, are fluorescence, phosphorescence or luminescence signals.

7. A method as claimed in claim 1 wherein the label used for the reference reagent is the same as that carried by the labelled ancillary reagent(s).

8. A method as claimed in claim 1, the assay being a competition assay, wherein in steps i) and ii) either a) a labelled ligand analogue is present as a labelled ancillary reagent and the measurement reagent (or optionally a reagent precomplexed with or capable of forming a complex involving the measurement reagent) is a specific binding partner for the ligand under assay or b) a labelled specific binding partner for the ligand under assay is present as a labelled ancillary reagent and the measurement reagent (or optionally a reagent precomplexed with or capable of forming a complex involving the measurement reagent) is a ligand analogue.

9. A method as claimed in claim 1, the assay being a sandwich assay, wherein in step i) and ii) a labelled specific binding partner for the ligand under assay is present as a labelled ancillary reagent and the measurement reagent (or optionally a reagent precomplexed with or capable of forming a complex involving the measurement reagent) is a further specific binding partner for the ligand under assay, said further specific binding partner being directed to an epitope of the ligand under assay different to the epitope to which the labelled specific binding partner is directed.

10. A biosensor device comprising a measurement surface carrying a directly or indirectly measurement reagent appropriate to an assay and which additionally carries an amount of a directly or indirectly immobilised reference reagent which gives rise to a reference signal, independent of the amount of ligand present in the sample, at the measurement surface.

11. A biosensor device as claimed in claim 10 wherein the device is additionally provided with one or more calibration surface(s) separate from the measurement surface, each calibration surface carrying an immobilised calibration reagent appropriate to the assay, the calibration reagent either being such to give rise to a zero or non-zero signal or being such as to form a complex involving at least one of a ligand and a labelled ancillary reagent(s) whereby any such complex gives rise to a non-zero signal (or, where no such complex is formed, which would be formed if ligand were present), the signal being either a function of or independent of the amount of ligand (if any) present in the sample.

12. A device as claimed in claim 10, being a specifically-reactive sample-collecting and testing device possessing a cavity or cavities, one surface of each cavity having a zone I carrying a layer comprising, in releasable form, labelled ancillary reagent(s) suitable for the desired assay, said surface being a surface of a first solid plate fashioned of transparent material, wherein the wall of each cavity opposite to said first plate comprises a second plate fashioned of transparent material and acts as a light-transmissive waveguide, the second plate having on its surface adjacent the cavity a zone II corresponding in orientation to the aforementioned zone I, zone II carrying a layer comprising, randomly distributed, an immobilised measurement reagent and an immobilised reference reagent, suitable for a desired assay.

13. A device as claimed in claim 12, additionally carrying on said first plate one or more further zone(s) carrying a layer comprising, in soluble releasable form, labelled ancillary reagent(s) suitable for the desired assay and additionally carrying on said second plate one or more further zone(s) each of which is corresponding in orientation to one of said further zone(s) on said first plate, and each of which is carrying a layer comprising an immobilised calibration reagent, the calibration reagent either being such to give rise to a zero or non-zero signal or being such as to form a complex involving at least one of a ligand and a labelled ancillary reagent(s) whereby any such complex gives rise to a non-zero signal (or, where no such complex is formed, which would be formed if ligand were present), the signal being either a second function of or independent of the amount of ligand (if any) present in the sample.

14. A device as claimed in claim 12 wherein the first plate carries on its surface remote from the cavity a layer of light-absorbing or opaque material.

15. Apparatus which comprises a device as claimed in claim 10; a source of radiation capable of being arranged such that, in use, radiation enters said device such that optically labelled species in the device are excited; and means for monitoring the emerging radiation.

16. A kit for performing a method of assay comprising a device as claimed in claim 10 together with appropriate labelled ancillary reagents.

17. A method of manufacturing specifically-reactive sample-collecting and testing devices possessing a cavity or cavities, one surface of each cavity having a zone I carrying a layer comprising, in releasable form, labelled ancillary reagent(s) suitable for the desired assay, said surface being a surface of a first solid plate fashioned of transparent material, wherein the wall of the or each cavity opposite to said first plate comprises a second plate fashioned of transparent material and acts as a light-transmissive waveguide, the second plate having on its surface adjacent the cavity a zone II corresponding in orientation to the aforementioned zone I, zone II carrying a layer comprising, randomly distributed, an immobilised measurement reagent and an immobilised reference reagent suitable for the desired assay comprising the steps of (a) forming a patch of suitable reagent(s), carried by zone I on the surface of a sheet material which is to provide part of a multiplicity of the devices, (b) forming a patch of suitable reagent(s), carried by zone II on the surface of an additional structure, involving immobilisation of the measurement reagent and reference reagent, said additional structure together with said sheet material providing for each of the multiplicity of devices a cavity for collecting and retaining a volume of sample liquid in contact with said layers of suitable reagents, and (c) separating the sheet material together with the additional structure into portions each providing one or a plurality of the sample-collecting and testing devices.

18. A method of manufacturing specifically-reactive sample-collecting and testing devices as claimed in claim 17, including the additional steps of forming the patch of suitable reagents in the further zone(s) on the surface of the sheet material and immobilizing a calibration reagent in the further zone(s) on the surface of the additional structure, the calibration reagent either being such to give rise to a zero or non-zero signal or being such as to form a complex involving at least one of a ligand and a labelled ancillary reagent(s) whereby any such complex gives rise to a non-zero signal (or, where no such complex is formed, which would be formed if ligand were present), the signal being either a second function of or independent of the amount of ligand (if any) present in the sample.

19. A method of manufacturing specifically-reactive sample-collecting and testing devices as claimed in claim 17, wherein the cavity is of capillary dimension.

* * * * *